United States Patent
Hamamoto et al.

(10) Patent No.: US 10,233,305 B2
(45) Date of Patent: Mar. 19, 2019

(54) MAGNESIUM HYDROXIDE-BASED SOLID SOLUTION, AND RESIN COMPOSITION AND PRECURSOR FOR HIGHLY ACTIVE MAGNESIUM OXIDE WHICH INCLUDE SAME

(71) Applicant: KYOWA CHEMICAL INDUSTRY CO., LTD., Takamatsu-shi, Kagawa (JP)

(72) Inventors: Yuya Hamamoto, Sakaide (JP); Daisuke Kudo, Sakaide (JP); Shigeo Miyata, Kitakyushu (JP)

(73) Assignee: KYOWA CHEMICAL INDUSTRY CO., LTD., Kagawa (JP)

( * ) Notice: Subject to any disclaimer, the term of this patent is extended or adjusted under 35 U.S.C. 154(b) by 20 days.

(21) Appl. No.: 15/506,454

(22) PCT Filed: Aug. 25, 2015

(86) PCT No.: PCT/JP2015/073802
§ 371 (c)(1),
(2) Date: Feb. 24, 2017

(87) PCT Pub. No.: WO2016/031803
PCT Pub. Date: Mar. 3, 2016

(65) Prior Publication Data
US 2017/0260356 A1 Sep. 14, 2017

(30) Foreign Application Priority Data
Aug. 26, 2014 (JP) .................. 2014-171103

(51) Int. Cl.
| | |
|---|---|
| *C01F 5/14* | (2006.01) |
| *C01F 5/22* | (2006.01) |
| *C08K 5/098* | (2006.01) |
| *C07C 53/06* | (2006.01) |
| *C07C 59/06* | (2006.01) |
| *C07C 59/08* | (2006.01) |
| *C08K 3/22* | (2006.01) |
| *C09K 21/02* | (2006.01) |
| *C09K 21/06* | (2006.01) |
| *C08L 23/00* | (2006.01) |
| *C08L 101/00* | (2006.01) |

(52) U.S. Cl.
CPC .............. *C08K 5/098* (2013.01); *C07C 53/06* (2013.01); *C07C 59/06* (2013.01); *C07C 59/08* (2013.01); *C08K 3/22* (2013.01); *C08L 23/00* (2013.01); *C08L 101/00* (2013.01); *C09K 21/02* (2013.01); *C09K 21/06* (2013.01); *C01F 5/14* (2013.01); *C01F 5/22* (2013.01)

(58) Field of Classification Search
None
See application file for complete search history.

(56) References Cited

U.S. PATENT DOCUMENTS

| | | | |
|---|---|---|---|
| 4,098,762 A | 7/1978 | Miyata et al. | |
| 6,025,424 A | 2/2000 | Katsuki et al. | |
| 7,686,986 B2 * | 3/2010 | Zhou ................ | C09K 21/02 106/18.26 |
| 2013/0041081 A1 | 2/2013 | Iwamoto et al. | |
| 2014/0186622 A1 * | 7/2014 | Kudo ................ | C01F 5/14 428/372 |
| 2015/0005429 A1 * | 1/2015 | Nakamura .......... | C01F 5/14 524/436 |
| 2015/0376507 A1 | 12/2015 | Matsui | |

FOREIGN PATENT DOCUMENTS

| | | |
|---|---|---|
| JP | 52-115799 A | 9/1977 |
| JP | 60-54915 A | 3/1985 |
| JP | 63-277511 A | 11/1988 |
| JP | 63277511 A * | 11/1988 |
| JP | 4-10330 A | 1/1992 |
| JP | 11-349592 A | 12/1999 |
| JP | 11349592 A * | 12/1999 |
| JP | 4157560 B2 | 10/2008 |
| WO | 2011/111487 A1 | 9/2011 |
| WO | WO2013/154200 A1 | 10/2013 |
| WO | 2014/128993 A1 | 8/2014 |

OTHER PUBLICATIONS

Yan et al., "Synthesis and characterization of novel organic magnesium salt flame retardant", Materials Letters, vol. 134, pp. 210-213, Jul. 19, 2014.
International Search Report dated Nov. 17, 2015, issued in counterpart International Application No. PCT/JP2015/073802 (2 pages).

* cited by examiner

*Primary Examiner* — Richard A Huhn
(74) *Attorney, Agent, or Firm* — Westerman, Hattori, Daniels & Adrian, LLP

(57) ABSTRACT

[Problem] To provide a magnesium hydroxide-based solid solution which has smaller primary particles and secondary particles and improved reactivity with an acid as compared with conventional magnesium hydroxide ($Mg(OH)_2$), improves the flame retardancy and mechanical strength of a resin, and also forms a non-sedimenting slurry, providing the same handleability as a liquid.
[Structure] A magnesium hydroxide-based solid solution represented by the following formula (1): $Mg(OH)_{2-x}R_x$ (Formula 1), wherein R represents a monovalent organic acid, and x represents $0<x<1$. The magnesium hydroxide-based solid solution is a magnesium oxide (MgO) precursor. A flame retardant for a synthetic resin, including the magnesium hydroxide-based solid solution as an active ingredient. A synthetic resin composition characterized by including 0.1 to 50 parts by weight of the magnesium hydroxide-based solid solution (b) per 100 parts by weight of a synthetic resin (a); and a molded article thereof.

9 Claims, 4 Drawing Sheets

MAGNESIUM HYDROXIDE-BASED SOLID SOLUTION, AND RESIN COMPOSITION AND PRECURSOR FOR HIGHLY ACTIVE MAGNESIUM OXIDE WHICH INCLUDE SAME

TECHNICAL FIELD

The present invention relates to a novel magnesium hydroxide-based solid solution represented by the following formula (1), a reinforcing agent and a flame retardant for a synthetic resin containing the magnesium hydroxide-based solid solution as an active ingredient, a synthetic resin composition, and a precursor of highly active magnesium oxide.

$$Mg(OH)_{2-x}R_x \quad \text{(Formula 1)}$$

(In the formula, R represents a monovalent organic acid, and x represents $0<x<1$.)

BACKGROUND ART

Magnesium hydroxide has been used in various fields, including applications to an antacid (stomach acid neutralizer), a laxative, a vinyl chloride stabilizer, a ceramic raw material, a heavy oil additive, a flue gas desulfurization agent, a magnesia fertilizer, a food additive (magnesium enhancer), as well as a flame retardant for resins taking advantage of its physical characteristics (utilization of endothermicity at the time of thermal decomposition).

For example, in order to satisfy the flame retardancy requirements for synthetic resins, magnesium hydroxide particles have been attracting attentions. Magnesium hydroxide particles are advantageous in that they have a dehydration onset temperature of about 340° C. and thus are applicable to almost any resin. Further, in PTL 1, a method for synthesizing novel and well crystal-grown magnesium hydroxide particles has been developed. Accordingly, using such a method, it has become possible to obtain an excellent molded article. PTL 1 proposes magnesium hydroxide particles having specific properties such that, as compared with conventional magnesium hydroxide particles, they have less structural distortion, less secondary aggregation of particles, and less residual water molecules and air. It is described that such magnesium hydroxide particles have high affinity with resins such as polyolefins and do not form silver streaks during molding, and thus a molded article with excellent appearance can be obtained, and also that a flame-retardant polypropylene resin molded article that satisfies V-0 of UL94 VE can be obtained.

In addition, PTL 2 proposes a technology in which a flame retardant including magnesium hydroxide particles having an average secondary particle size of 0.4 to 1.0 μm as measured by a laser diffraction scattering method, is used for a polyolefin or a copolymer thereof. PTL 3 proposes a technology in which a certain amount of magnesium hydroxide having an average secondary particle size of 0.01 to 10 μm as measured by a laser diffraction scattering method is blended with hydrotalcite compound particles having specific properties, thereby imparting a suppressing effect on carbon dioxide gas bubbling.

CITATION LIST

Patent Literature

PTL 1: JP-A-52-115799
PTL 2: Japan Patent No. 4157560
PTL 3: WO2011/111487
PTL 4: JP-A-4-10330

SUMMARY OF INVENTION

Technical Problem

However, in conventional magnesium hydroxide, primary particles and secondary particles are relatively large. Accordingly, in various application fields, their performance has not been satisfied yet. Primary particles can be compared in terms of BET specific surface area, and the primary particle size of conventional magnesium hydroxide is 50 m²/g or less. In addition, conventional magnesium hydroxide settles in a liquid medium and is also opaque. Accordingly, it is not possible to produce a highly transparent liquid-form product, which is easier to handle than a powder-form, and can also be expected to improve performance.

Thus, an object of the invention is to provide a magnesium hydroxide-based compound, whose primary particles can be made smaller than those of conventional magnesium hydroxide, and which is in the form of nearly monodispersed and nano-level fine particles. Another object is to provide a magnesium hydroxide-based compound having a lower dehydration onset temperature than $Mg(OH)_2$, which is expected to improve flame retardancy. Still another object is to produce a highly transparent liquid-form product with nano-level highly dispersed fine particles.

Solution to Problem

The inventors of the present invention have found that in a conventional production method in which an alkali such as NaOH or $Ca(OH)_2$ is added to an aqueous solution of a water-soluble magnesium salt such as $MgCl_2$ to produce magnesium hydroxide, when at least one of formic acid, glycolic acid, and lactic acid which compete with OH— from the alkali, is additionally added and reacted, the magnesium hydroxide-based solid solution represented by the following formula of the invention having OH in magnesium hydroxide $(Mg(OH)_2)$ is partially substituted with at least one of formic acid, glycolic acid, and lactic acid, can be obtained.

$$Mg(OH)_{2-x}R_x \quad \text{(Formula 1)}$$

In the formula, R represents a monovalent organic acid, and x represents $0<x<1$, preferably $0<x\leq0.2$. In the case where x is more than 1, the solubility limit of the monovalent organic acid in magnesium hydroxide is exceeded.

The subject matter of the invention relates to the magnesium hydroxide-based solid solutions defined in the following (1) to (7).

(1) A magnesium hydroxide-based solid solution represented by the following formula (1):

$$Mg(OH)_{2-x}R_x \quad \text{(Formula 1)}$$

wherein R represents a monovalent organic acid, and x represents $0<x<1$.
(2) The magnesium hydroxide-based solid solution according to (1), wherein x is $0<x\leq0.2$.
(3) The magnesium hydroxide-based solid solution according to (1) or (2), wherein the monovalent organic acid is at least one of formic acid, glycolic acid, and lactic acid.
(4) The magnesium hydroxide-based solid solution according to any one of (1) to (3), having an average secondary particle size of 200 nm or less.

(5) The magnesium hydroxide-based solid solution according to any one of (1) to (4), having a dehydration onset temperature of about 300° C.
(6) The magnesium hydroxide-based solid solution according to any one of (1) to (5), being surface-treated with at least one surface treatment agent selected from the group consisting of higher fatty acids, alkali metal salts of higher fatty acids, anionic surfactants, phosphates, silane-based, titanate-based, or aluminum-based coupling agents, esters of polyhydric alcohols and fatty acids, sulfates of higher alcohols, silicon compounds, phosphorus-based compounds, aluminum-based compounds, inorganic acids, organic acids, and silicone.
(7) The magnesium hydroxide-based solid solution according to any one of (1) to (6), being a magnesium oxide (MgO) precursor.

The subject matter of the invention also relates to the flame retardant for a synthetic resin defined in the following (8) and the synthetic resin compositions and a molded article thereof defined in (9) and (10).
(8) A flame retardant for a synthetic resin, including the magnesium hydroxide-based solid solution according to any one of (1) to (6) as an active ingredient.
(9) A synthetic resin composition including 0.1 to 50 parts by weight of the magnesium hydroxide-based solid solution according to any one of (1) to (6) (b), and 100 parts by weight of a synthetic resin (a); and a molded article thereof.
(10) The synthetic resin composition according to (9), wherein the synthetic resin is a polyolefin or a copolymer thereof; and a molded article thereof.

Advantageous Effects of Invention

The magnesium hydroxide-based solid solution of the invention is represented by the following formula 1, and the primary particles and secondary particles thereof can be made smaller than those of conventional magnesium hydroxide ($Mg(OH)_2$). As a result, the reactivity with an acid is improved, and such a solid solution improves the flame retardancy and mechanical strength of a resin. In addition, the solid solution forms a non-settling slurry, providing the same handleability like a liquid. Further, the dehydration onset temperature becomes lower than that of $Mg(OH)_2$, resulting in improved flame retardancy. In addition, the solid solution is useful as a precursor of nano-level highly dispersed fine particles of MgO.

   (Formula 1)

(In the formula, R is a monovalent organic acid, and x is 0<x<1.)

DESCRIPTION OF EMBODIMENTS

Figure 1:
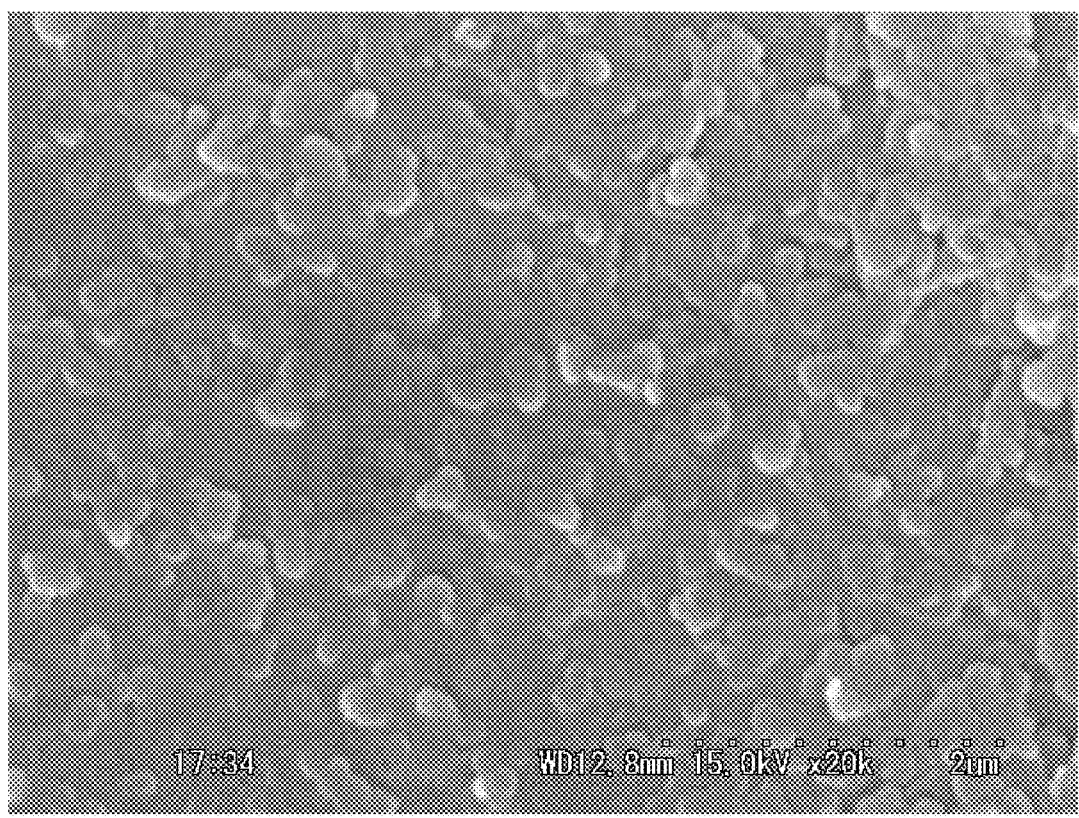
FIG. 1 is a SEM for Sample 1.

The production of the magnesium hydroxide-based solid solution of the invention is as follows. In a conventional magnesium hydroxide production method in which an alkali such as NaOH or $Ca(OH)_2$ is added to an aqueous solution of a water-soluble magnesium salt such as $MgCl_2$, at least one of formic acid, glycolic acid, and lactic acid, which compete with OH— from the alkali, is additionally added and reacted. As a result, the magnesium hydroxide-based solid solution of the invention, having OH in magnesium hydroxide ($Mg(OH)_2$) partially substituted with at least one of formic acid, glycolic acid, and lactic acid, can be obtained.

In the magnesium hydroxide-based solid solution represented by the following formula of the invention, OH in $Mg(OH)_2$ is partially substituted with a monocarboxylic acid or a monooxycarboxylic acid, whereby the growth of primary particles can be significantly suppressed. The reason therefor is as follows. When the above monocarboxylic acid having a greater ionic diameter than an OH group and a stronger chemical bonding force with Mg than OH is present at the time of the reaction, its presence functions to suppress or inhibit the crystal growth of $Mg(OH)_2$, which is structurally similar to the closest packing in the c-axis direction of the OH group. As a result, the primary particles can be made smaller than those of conventional magnesium hydroxide, and, at the same time, it becomes possible to synthesis nearly monodispersed, nano-level fine particles by a hydrothermal treatment. Further, because the dehydration onset temperature becomes lower than that of $Mg(OH)_2$, improvement in flame retardancy can be expected. In addition, by further subjecting the hydrothermal treated product to a wet pulverization treatment using a bead mill or the like, nano-level highly dispersed fine particles can be produced, making it possible to produce a highly transparent liquid-form product.

   (Formula 1)

(In the formula, R represents a monovalent organic acid, and x represents 0<x<1.)

Primary particles of the solid solution of the invention are significantly smaller than in a conventional method, and a BET specific surface area of 100 $m^2/g$ or more can also be easily achieved. The solid solution of the invention can be formed into nano-level fine particles having a secondary particle size of 0.3 μm or less, or further 0.1 μm or less, by wet grinding such as a bead mill treatment or by a hydrothermal treatment at about 150° C. or less. In addition, a non-settling, highly transparent slurry (liquid-form) can be produced. In addition, it is also possible to make the dehydration onset temperature upon decomposition 40 to 50° C. lower than that of $Mg(OH)_2$.

The magnesium hydroxide-based solid solution of the invention has the above mentioned characteristics, and is quite similar to conventional magnesium hydroxide in other properties, and thus can be applied to the conventional application fields without any problems.

The average secondary particle size of the magnesium hydroxide-based solid solution of the invention is 300 nm or less, preferably 200 nm or less, and still more preferably 100 nm or less.

The magnesium hydroxide-based solid solution of the invention has an average secondary particle size of 300 nm or less, preferably 200 nm or less, and still more preferably 100 nm or less, and thus it can be a precursor of highly active magnesium oxide (MgO) and can be applicable in various fields where MgO has been used. As the precursors, for example, one or more of the following compounds are already known: magnesium alkoxide ($Mg(OR)_2$), magnesium acetylacetone ($Mg(acac)_2$), magnesium hydroxide ($Mg(OH)_2$), magnesium carbonate ($MgCO_2$), magnesium chloride ($MgCl_2$), magnesium sulfate ($MgSO_4$), magnesium nitrate ($Mg(NO_3)_2$), and oxalate magnesium ($MgC_2O_4$). Some compounds may be usually in the form of hydrates. The hydrates may also be used as a precursor. A magnesium oxide (MgO) precursor can be used as follows, for example. After forming a porous semiconductor layer, a precursor solution of MgO, which is an insulating oxide, is applied to the porous semiconductor layer from the surface side, and followed by a heat treatment. By such a method, the surface of the porous semiconductor layer on the catalyst layer side (including the inner surface of pores) is covered with MgO, thereby producing a photoelectric transducer. In addition, the formation of an MgO film to serve as a protective layer can be performed by a thin-film forming method such as a vacuum deposition method, an EB method, or a sputtering method, or alternatively by a printing method using an organic material which is a precursor of MgO (thick-film forming method). Among them, in a printing method, for example, as disclosed in PTL 4, a liquid organic material and a glass material are mixed, and the mixture is applied to a panel glass surface by spin coating and then calcined at near 600° C., thereby crystallized MgO forms a protective layer. As compared with a vacuum deposition method, an EB method, and a sputtering method, the printing method is advantageous in that the process is relatively simple and can be performed at low cost. In addition, because there is no need to use a vacuum process, the method is also excellent in terms of throughput.

<Surface Treatment>

In the case where the magnesium hydroxide-based solid solution of the invention is combined with a resin, it is preferable to perform a surface treatment. Examples of surface treatment agents include anionic surfactants such as higher fatty acids, phosphates, silane coupling agents, titanate coupling agents, aluminum coupling agents, and silicone. It is preferable that the surface treatment agent is used in an amount of 1 to 20 wt % relative to magnesium hydroxide.

It is preferable that the surface treatment is performed by a wet or a dry process. The wet process is a method in which a magnesium hydroxide-based solid solution is dispersed in a solvent such as water or alcohol, and then a surface treatment agent is added with stirring. The dry process is a method in which a surface treatment agent is added to a magnesium hydroxide-based solid solution in powder form with stirring using a high-speed stirrer, such as a Henschel mixer.

Examples of materials preferably used as surface treatment agents are as follows: (a) higher fatty acid groups having 10 or more carbon atoms, such as stearic acid, erucic acid, palmitic acid, lauric acid, and behenic acid, (b) alkali metal salts of the higher fatty acids, (c) anionic surfactants such as polyethylene glycol sulfates, amide-linked sulfates, ester-linked sulfates, ester-linked sulfonates, amide-linked sulfonates, ether-linked sulfonates, ether-linked alkylarylsulfonates, ester-linked alkylarylsulfonates, and amide-linked alkylarylsulfonates of polyethylene glycol ether, (d) monoesters and/or diesters of orthophosphoric acid and oleyl alcohol, stearyl alcohol or the like, as well as mixtures thereof, which are in the form of acids or phosphates such as alkali metal salts and amine salts, (e) silane coupling agents such as vinylethoxysilane, vinyl-tris(2-methoxyethoxy)silane, γ-methacryloxypropyltrimethoxysilane, γ-aminopropyltrimethoxysilane, β(3,4-epoxycyclohexyl) ethyltrimethoxysilane, γ-glycidoxypropyltrimethoxysilane, and γ-mercaptopropyltrimethoxysilane; titanate-based coupling agents such as isopropyl isostearoyl titanate, isopropyl tris(dioctylpyrophosphate) titanate, isopropyl tris(N-aminoethyl-aminoethyl) titanate, and isopropyl tridecylbenzenesulfonyl titanate; and aluminate-based coupling agents such as acetoalkoxyaluminum diisopropylates, (f) esters of polyhydric alcohols and fatty acids, such as glycerol monostearate and glycerin monooleate, (g) sulfates of higher alcohols such as stearyl alcohol and oleyl alcohol, and (h) silicon compounds, phosphorus-based compounds, and aluminum-based compounds having $SiO(OH)_3^-$, $Al(OH)_4^-$, $Cl^-$, $NO_3^-$, $H_2PO_4^-$, $C_6H_7O_7^-$, $SiO_2(OH)_2^{2-}$, $Si_2O_6(OH)_6^{2-}$, $HPO_4^{2-}$, $C_6H_6O_7^{2-}$, $PO_4^{3-}$, $C_6H_5O_7^3$, $SiO_4^{4-}$, $Si_4O_8(OH)_4^{4-}$.

As necessary, the surface-treated magnesium hydroxide particles may be subjected to suitably selected means, such as washing with water, dehydration, granulation, drying, grinding, and classification, and thus formed into a final product.

<Method for Producing Magnesium Hydroxide-Based Solid Solution>

Magnesium hydroxide-based solid solution is produced by the following methods.

(A) To a mixed aqueous solution of a water-soluble magnesium salt and a monovalent organic acid or a salt thereof, an alkali in an amount almost equivalent to Mg is added to cause coprecipitation. Subsequently, as necessary, the reaction product slurry is heated and aged. The slurry is preferably subjected to a hydrothermal treatment at 100° C. or more.

(B) To magnesium hydroxide prepared by adding an aqueous solution of an alkali to an aqueous solution of a water-soluble magnesium salt to cause coprecipitation, a monovalent organic acid or a salt thereof is added, and the mixture is subjected to a hydrothermal treatment at 100° C. or more.

(C) The solid solution obtained by the method (A) and/or (B) is Subjected a wet grinding treatment using a bead mill, thereby further reducing the size of secondary particles.

Examples of water-soluble magnesium salts include magnesium chloride, magnesium nitrate, magnesium sulfate, and magnesium acetate.

Examples of alkalis include alkali metal hydroxides such as sodium hydroxide and potassium hydroxide, alkaline earth metal hydroxides such as calcium hydroxide, and ammonium hydroxide.

Examples of monovalent organic acids include formic acid, glycolic acid, and lactic acid, and salts thereof, which include water-soluble salts such as a sodium salt and a potassium salt.

The hydrothermal treatment is performed at 100° C. or more, preferably 105° C. to 150° C., and more preferably 110° C. to 130° C. The treatment time is preferably 1 to 20 hours.

After the hydrothermal treatment, commonly used processes such as filtration, washing with water, emulsification, surface treatment, filtration, drying, grinding, and classification are suitably selected and performed, whereby the magnesium hydroxide-based solid solution of the invention can be produced.

(Resin Composition)

The resin composition of the invention is prepared by blending the magnesium hydroxide-based solid solution in an amount of 0.1 to 100 parts by weight, preferably 1 to 50 parts by weight, per 100 parts by weight of a resin.

The method for mixing and kneading a resin and the magnesium hydroxide-based solid solution of the invention is not particularly limited, and may be any method as long as the two materials can be uniformly mixed. For example, mixing and kneading are performed using a single-screw or twin-screw extruder, a roll, a Banbury mixer. The molding method is not particularly limited either. According to the material of resin or rubber, the molded article to be obtained, any of molding means known per se may be employed. Examples of the molding means include injection molding, extrusion molding, blow molding, press molding, rotation molding, calendar molding, sheet-forming molding, transfer molding, lamination molding, and vacuum molding.

The synthetic resin to be blended with the magnesium hydroxide-based solid solution of the invention is selected from any resins and/or rubbers, and may be any of those usually used as molded articles. Examples of the synthetic resin include thermoplastic resins such as polymers and copolymers of $C_2$ to $C_8$ olefins ($\alpha$-olefin) including polyethylene, polypropylene, an ethylene/propylene copolymer, polybutene, poly-4-methylpentene-1, copolymers of these olefins and diene, an ethylene-acrylate copolymer, polystyrene, an ABS resin, an AAS resin, an AS resin, an MBS resin, an ethylene/vinyl chloride copolymer resin, an ethylene-vinyl acetate copolymer resin, an ethylene-vinyl chloride-vinyl acetate graft polymer resin, polyvinylidene chloride, polyvinyl chloride, chlorinated polyethylene, chlorinated polypropylene, a vinyl chloride-propylene copolymer, polyvinyl acetate, a phenoxy resin, polyacetal, polyamide, polyimide, polycarbonate, polysulfone, polyphenylene oxide, polyphenylene sulfide, polyethylene terephthalate, polybutylene terephthalate, and a methacrylic resin.

Among these thermoplastic resins, polyolefin and copolymers thereof are preferable. Specific examples thereof include polypropylene resins such as a polypropylene homopolymer and an ethylene-propylene copolymer, polyethylene resins such as high density polyethylene, low density polyethylene, linear low density polyethylene, ultralow density polyethylene, EVA (ethylene-vinyl acetate resin), EEA (ethylene-ethyl acrylate resin), EMA (ethylene-methyl acrylate copolymer resin), EAA (ethylene-acrylate copolymer resin), and ultrahigh molecular weight polyethylene, and polymers and copolymers of $C_2$ to $C_6$ olefins ($\alpha$-ethylene) such as polybutene and poly(4-methylpentene-1).

Examples further include thermosetting resins, such as an epoxy resin, a phenol resin, a melamine resin, an unsaturated polyester resin, an alkyd resin, and an urea resin, and synthetic rubbers, such as EPDM, an butyl rubber, isoprene rubber, SBR, NBR, chlorosulfonated polyethylene, NIR, a urethane rubber, a butadiene rubber, an acrylic rubber, a silicone rubber, and a fluororubber.

The resin composition of the invention is substantially formed of the synthetic resin and the magnesium hydroxide-based solid solution, but it is also possible to further blend a flame retardant synergist in a small proportion. By blending a flame retardant synergist, the proportion of the magnesium hydroxide-based solid solution in the resin can be further reduced, and also the flame-retardant effect can be increased.

It is preferable that the flame retardant synergist is red phosphorus, a carbon powder, or a mixture thereof. As red phosphorus, in addition to ordinary red phosphorus for flame retardants, it is also possible to use red phosphorus surface-coated with a thermosetting resin, a polyolefin, a carboxylic polymer, titanium oxide, or a titanium-aluminum condensate, for example. In addition, examples of carbon powders include carbon black, activated carbon, and graphite. Such carbon black may be prepared by any of an oil furnace method, a gas furnace method, a channel method, a thermal method, and an acetylene method.

In the case where a flame retardant synergist is blended, it is suitable that the proportion thereof is within a range of 0.5 to 20 wt %, preferably 1 to 15 wt %, relative to the total weight of the thermoplastic resin and the magnesium hydroxide-based solid solution. The resin composition of the invention may be prepared by mixing the synthetic resin, and the magnesium hydroxide-based solid solution, and optionally the flame retardant synergist in the above proportions by a means known per se.

In the resin composition of the invention, in addition to the magnesium hydroxide-based solid solution of the invention, conventionally known reinforcing agents such as talc, mica, glass fibers, and basic magnesium sulfate fibers may also be used. The amount of reinforcing agent blended is 1 to 50 parts by weight per 100 parts by weight of the resin.

Further, it is possible to suitably select and blend other commonly used additives, such as antioxidants, UV absorbers, lubricants, pigments such as carbon black, bromine-based or phosphate-based flame retardants, and fillers such as calcium carbonate.

The amounts of these additives blended per 100 parts by weight of the resin are as follows: antioxidant: 0.01 to 5 parts by weight, UV absorber: 0.01 to 5 parts by weight, lubricant: 0.1 to 5 parts by weight, pigment: 0.01 to 5 parts by weight, flame retardant: 0.1 to 100 parts by weight, filler: 1 to 50 parts by weight.

Hereinafter, the invention will be described in further detail through examples. However, the invention is not limited to these examples.

In the examples, the average secondary particle size (A), decomposition onset temperature (B), settleability (C), and total light transmission (transparency) (D) of a magnesium hydroxide-based solid solution were measured by the following method.

(A) Average Secondary Particle Size

The average secondary particle size is measured and determined using a MICROTRAC particle size distribution meter, SPA type (manufactured by LEEDS & NORTHRUP INSTRUMENTS).

700 mg of a powder sample is added to 70 ml of water and then ultrasonically dispersed (manufactured by NISSEI, MODEL US-300, current: 300 µA) for 3 minutes. Subsequently, 2 to 4 ml of the dispersion is taken and added to a sample chamber of the particle size distribution meter, which contains 250 ml of degassed water. The analyzer is operated to circulate the suspension for 8 minutes, and then the particle size distribution is measured. The distribution is measured twice in total, and the arithmetic average of the 50% cumulative secondary particle sizes obtained in the respective measurements is calculated and defined as the average secondary particle size of the sample.

(B) Decomposition Onset Temperature

The decomposition onset temperature is determined from TG-DTA in ambient atmosphere at a temperature rise rate of 5° C./min.

(C) Settleability

A suspension having a solid concentration of 25 g/L is placed in a 50-mL measuring cylinder, and the changes over time in the volume of the supernatant part are measured.

(D) Total Light Transmission (Transparency)

Measurement is performed in accordance with JIS K-7361.

Example 1

To a reaction tank 1 L in volume made of stainless steel containing 320 mL of a 1.5 mol/L magnesium chloride solution, 320 mL of a 3 mol/L sodium hydroxide solution was added with stirring to cause coprecipitation.

65 g of sodium formate was added to the suspension and mixed. Next, the suspension was aged in an autoclave 1 L in volume at 140° C. for 2 hours. After aging, the suspension was solid-liquid separated, washed, dehydrated, dried, and ground to give a sample 1. SEM for sample 1 is shown in FIG. 1.

Example 2

Figure 2:
FIG. 2 is a SEM for Sample 2.

To a reaction tank 1 L in volume made of stainless steel containing 154 mL of a 3 mol/L magnesium chloride solution and 0.93 g of sodium glycolate, ion-exchanged water was added to make 321.7 mL, thereby preparing a mixed solution. 280 mL of a 3.3 mol/L sodium hydroxide solution was added to the mixed solution with stirring to cause coprecipitation. Next, the suspension was aged in an autoclave 1 L in volume at 120° C. for hours. After aging, the suspension was solid-liquid separated, washed, dehydrated, dried, and ground to give a sample 2. SEM for sample 2 is shown in FIG. 2.

Example 3

Figure 3:
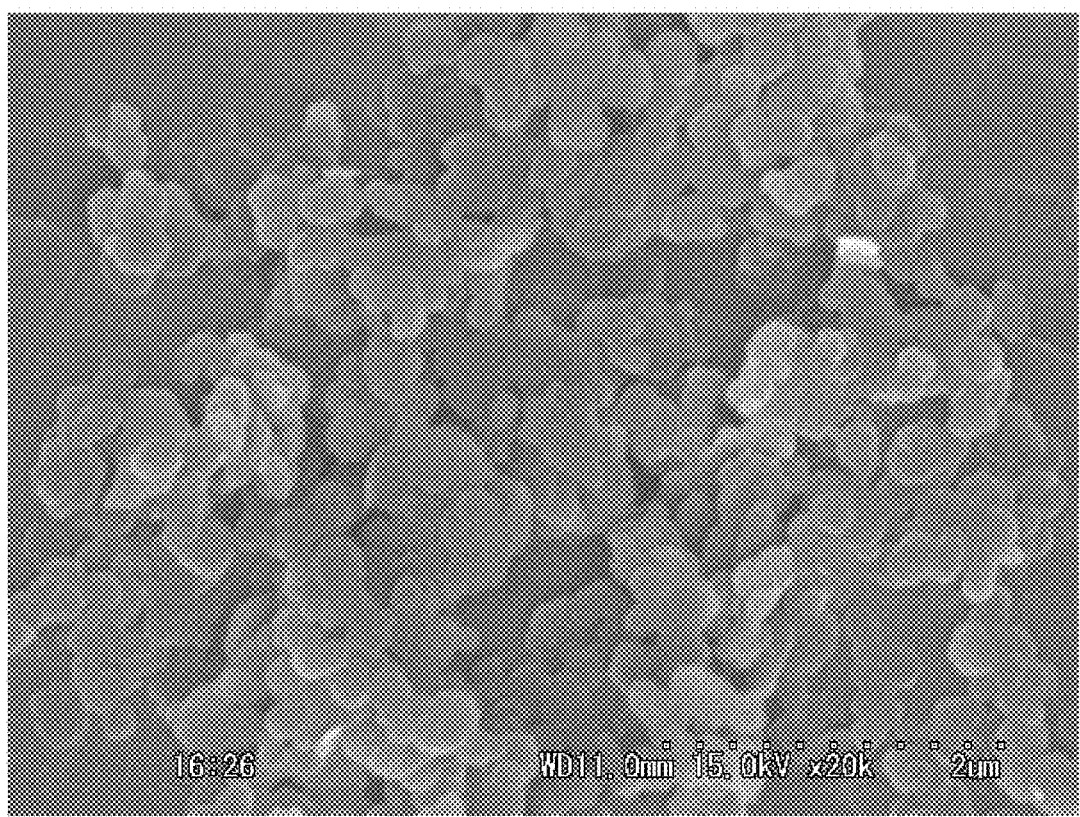
FIG. 3 is a SEM for Sample 3.

To a reaction tank 1 L in volume made of stainless steel containing 180 mL of a 3 mol/L magnesium chloride solution and 2.40 g of a 50% sodium lactate solution, ion-exchanged water was added to make 380.0 mL, thereby preparing a mixed solution. 360 mL of a 3 mol/L sodium hydroxide solution was added to the mixed solution with stirring to cause coprecipitation. The coprecipitate was aged in an autoclave 1 L in volume at 120° C. for 2 hours. After aging, the suspension was solid-liquid separated, washed, dehydrated, dried, and ground to give a sample 3 as a powder. SEM for sample 3 is shown in FIG. 3.

Example 4

The ground product obtained in Example 3 was dispersed in water using a homogenizer to give a sample 4 as a suspension. The coprecipitate suspension was wet-ground with zirconia beads having a diameter of 0.05 mm, thereby giving a sample 5 as a suspension having an average secondary particle size of 50 nm. Further, the suspension sample 5 was wet-ground with zirconia beads having a diameter of 0.03 mm, thereby giving a sample 6 as a suspension having an average secondary particle size of 20 nm. The settleability of each suspension was measured. The results are shown in Table 2.

Comparative Example 1

To a reaction tank 1 L in volume made of stainless steel containing 320 mL of a 1.5 mol/L magnesium chloride solution, 320 mL of a 3 mol/L sodium hydroxide solution was added with stirring, thereby preparing a magnesium hydroxide suspension.

Figure 4:
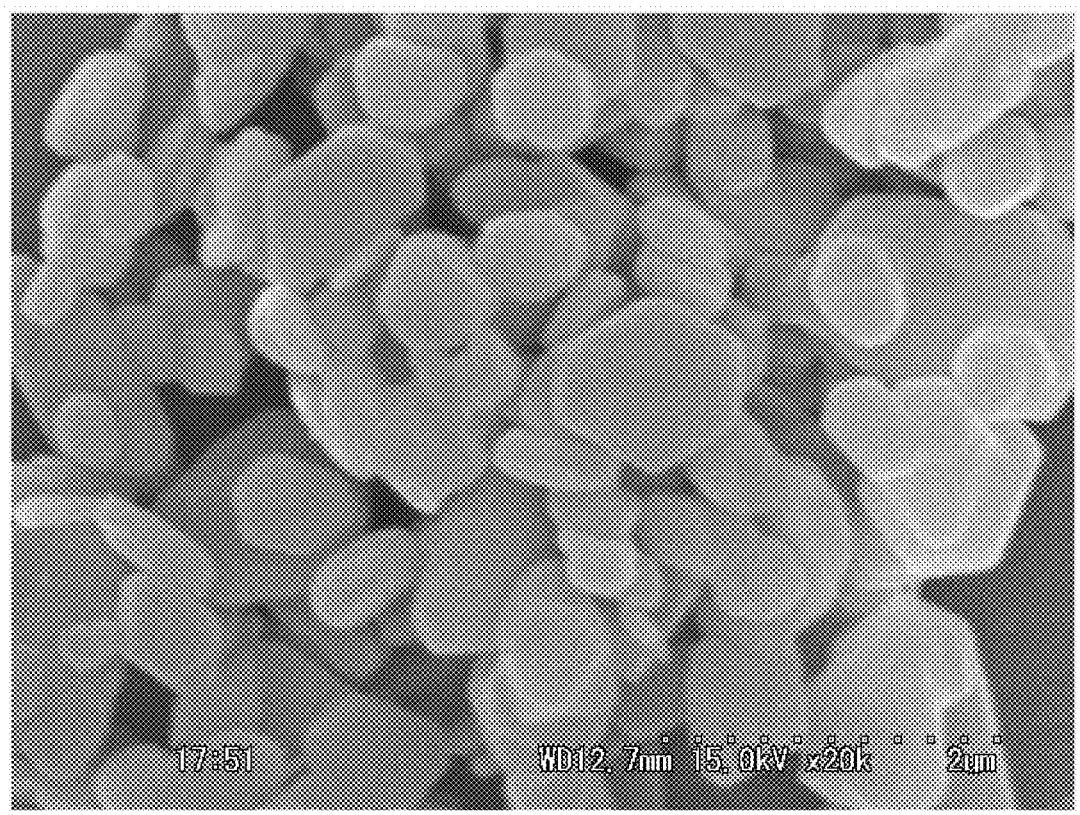
FIG. 4 is a SEM for Comparison 1.

The obtained suspension was aged in an autoclave 1 L in volume at 150° C. for 2 hours. After aging, the suspension was solid-liquid separated, washed, dehydrated, dried, and ground. SEM of comparison 1 is shown in FIG. 4.

TABLE 1

|  | Sample 1 | Sample 2 | Sample 3 | Comparison 1 |
|---|---|---|---|---|
| Average Secondary Particle Size [nm] | 124 | 203 | 231 | 693 |
| Composition | $Mg(OH)_{1.985}(HCOO)_{0.015}$ | $Mg(OH)_{1.995}(CH2(OH)COO)_{0.005}$ | $Mg(OH)_{1.999}(CH3CH(OH)COO)_{0.001}$ | $Mg(OH)_2$ |
| Decomposition Onset Temperature | 291.4° C. | 316.3° C. | 308.2° C. | 314.2° C. |

* Composition is calculated from the ratio between Mg concentration and organic acid concentration in a certain amount of powder sample dissolved in an acid.

TABLE 2

Settleability of Each Suspension (25 g/L)

|  | Sample 4 | Sample 5 | Sample 6 |
|---|---|---|---|
| After 1 day (After 24 hours) | 5 mL | 1 mL | 0 mL |
| After 5 days (After 96 hours) | 29 mL | 3 mL | 0 mL |
| After 10 days (After 240 hours) | 31 mL | 5 mL | 0 mL |

*Each value is the settled volume.

TABLE 3

Visible Light Transmission of Each Suspension (0.3 g/L)

|  | Sample 4 | Sample 6 | Comparative Example 1 |
|---|---|---|---|
| Average Transmission | 80.6% | 86.7% | 30.0% |

Each value is the average transmission of light having a wavelength of 380 to 780 nm.

INDUSTRIAL APPLICABILITY

In the magnesium hydroxide-based solid solution of the invention, the primary particles and secondary particles can be made smaller than those of conventional magnesium hydroxide [$Mg(OH)_2$]. As a result, the reactivity with an acid is improved, and such a solid solution improves the flame retardancy and mechanical strength of a resin. In addition, the solid solution forms a non-settling slurry, providing the same handleability as a liquid. Further, the dehydration onset temperature becomes lower than that of $Mg(OH)_2$, resulting in improved flame retardancy. In addition, the solid solution is useful as a precursor of nano-level highly dispersed fine particles of MgO.

Magnesium hydroxide has been used in various fields, including applications to an antacid (stomach acid neutralizer), a laxative, a vinyl chloride stabilizer, a ceramic raw material, a heavy oil additive, a flue gas desulfurization agent, a magnesia fertilizer, a food additive (magnesium enhancer), as well as a flame retardant for resins taking advantage of its physical characteristics (utilization of endothermicity at the time of thermal decomposition). However, because the primary particles and secondary particles thereof are relatively large, the limit of performance has been reached in various application fields. The invention solves the above problem, and further expansion of applications is expected.

The invention claimed is:

1. A magnesium hydroxide-based solid solution represented by the following formula (1):

$$Mg(OH)_{2-x}R_x \quad \text{(Formula 1)}$$

wherein R represents a monovalent organic acid, and x represents $0<x<1$, wherein the magnesium hydroxide-based solid solution has an average secondary particle size of 200 nm or less.

2. The magnesium hydroxide-based solid solution according to claim 1, wherein x is $0<x\leq0.2$.

3. The magnesium hydroxide-based solid solution according to claim 1, wherein the monovalent organic acid is at least one of formic acid, glycolic acid, and lactic acid.

4. The magnesium hydroxide-based solid solution according to claim 1, having a dehydration onset temperature of about 300° C.

5. The magnesium hydroxide-based solid solution according to claim 1, being surface-treated with at least one surface treatment agent selected from the group consisting of higher fatty acids, alkali metal salts of higher fatty acids, anionic surfactants, phosphates, silane-based, titanate-based, or aluminum-based coupling agents, esters of polyhydric alcohols and fatty acids, sulfates of higher alcohols, silicon compounds, phosphorus-based compounds, aluminum-based compounds, inorganic acids, organic acids, and silicones.

6. The magnesium hydroxide-based solid solution according to claim 1, being a magnesium oxide (MgO) precursor.

7. A flame retardant for a synthetic resin, comprising the magnesium hydroxide-based solid solution according to claim 1.

8. A synthetic resin composition comprising 0.1 to 50 parts by weight of the magnesium hydroxide-based solid solution according to claims 1 (b), and 100 parts by weight of a synthetic resin (a).

9. The synthetic resin composition according to claim 8, wherein the synthetic resin is a polyolefin or a copolymer thereof.

* * * * *